(12) United States Patent
Romoscanu et al.

(10) Patent No.: US 9,174,024 B1
(45) Date of Patent: Nov. 3, 2015

(54) STEERING CONTROL MECHANISMS FOR CATHETERS

(71) Applicant: Endosense SA, Geneva (CH)

(72) Inventors: Alexandre Ioan Romoscanu, Geneva (CH); Timothy J. Wood, Wilmington, MA (US)

(73) Assignee: ST. JUDE MEDICAL LUXEMBOURG HOLDINGS S.À.R.L., Luxembourg (LU)

( * ) Notice: Subject to any disclaimer, the term of this patent is extended or adjusted under 35 U.S.C. 154(b) by 333 days.

(21) Appl. No.: 13/842,349

(22) Filed: Mar. 15, 2013

(51) Int. Cl.
*A61M 25/00* (2006.01)
*A61M 25/01* (2006.01)

(52) U.S. Cl.
CPC ....... *A61M 25/0147* (2013.01); *A61M 25/0136* (2013.01)

(58) Field of Classification Search
CPC ..................... A61M 25/0147; A61M 25/0136; A61M 25/0144
See application file for complete search history.

(56) References Cited

U.S. PATENT DOCUMENTS

| | | | |
|---|---|---|---|
| 5,702,433 A * | 12/1997 | Taylor et al. | 607/101 |
| 2006/0200049 A1 | 9/2006 | Leo et al. | |
| 2007/0060847 A1 | 3/2007 | Leo et al. | |
| 2008/0009750 A1 | 1/2008 | Aeby et al. | |
| 2008/0294144 A1 | 11/2008 | Leo et al. | |
| 2009/0177095 A1 | 7/2009 | Aeby et al. | |
| 2009/0287092 A1 | 11/2009 | Leo et al. | |
| 2011/0251519 A1 | 10/2011 | Romoscanu | |
| 2011/0251554 A1 | 10/2011 | Romoscanu | |
| 2014/0276222 A1 * | 9/2014 | Tegg | 600/585 |
| 2014/0276645 A1 * | 9/2014 | Lam | 604/528 |

* cited by examiner

*Primary Examiner* — Nicholas Lucchesi
*Assistant Examiner* — Melissa A Snyder
(74) *Attorney, Agent, or Firm* — Dykema Gossett PLLC

(57) ABSTRACT

A steering handle for a catheter. The steering handle includes a thumb knob arrangement for driving a cam assembly that in turn actuates a pull wire or pull wires. In some embodiments, the cam assembly includes a set of dual pins that actuate the pull wire in a quasi-linear relationship between cam rotation and axial displacement of the wire. In certain embodiments, the second set of dual pins imparts a reverse action on a second pull wire, also in quasi-linear fashion. That is, when one wire is released by the cam assembly, the other wire is taken in by the cam assembly. In various embodiments, the quasi-linear action can cause release of more pull wire than is taken in, thereby helping prevent the released pull wire to act as an unwanted counter force to the actuated pull wire.

6 Claims, 8 Drawing Sheets

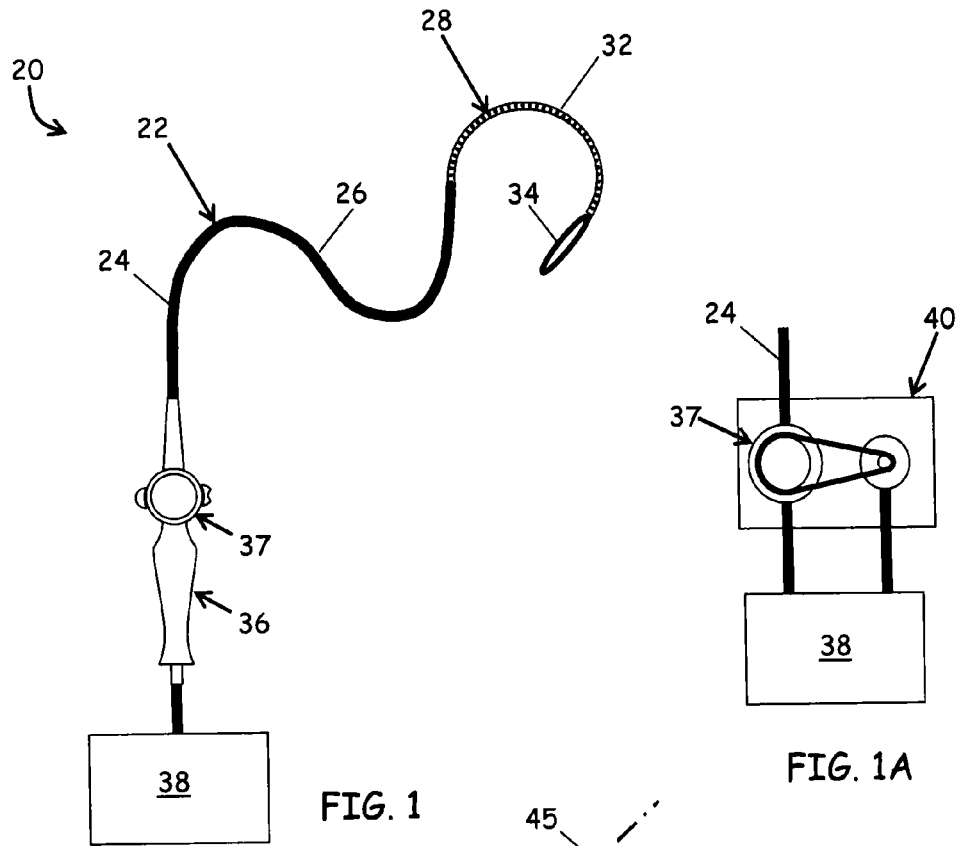
FIG. 1
FIG. 1A
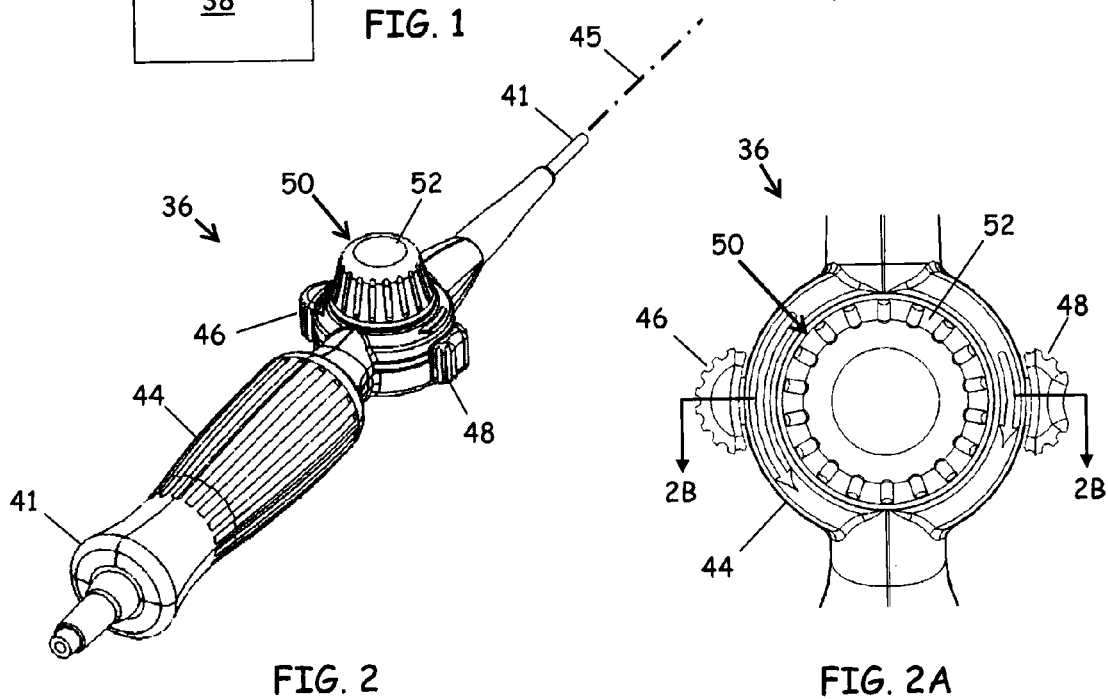
FIG. 2
FIG. 2A

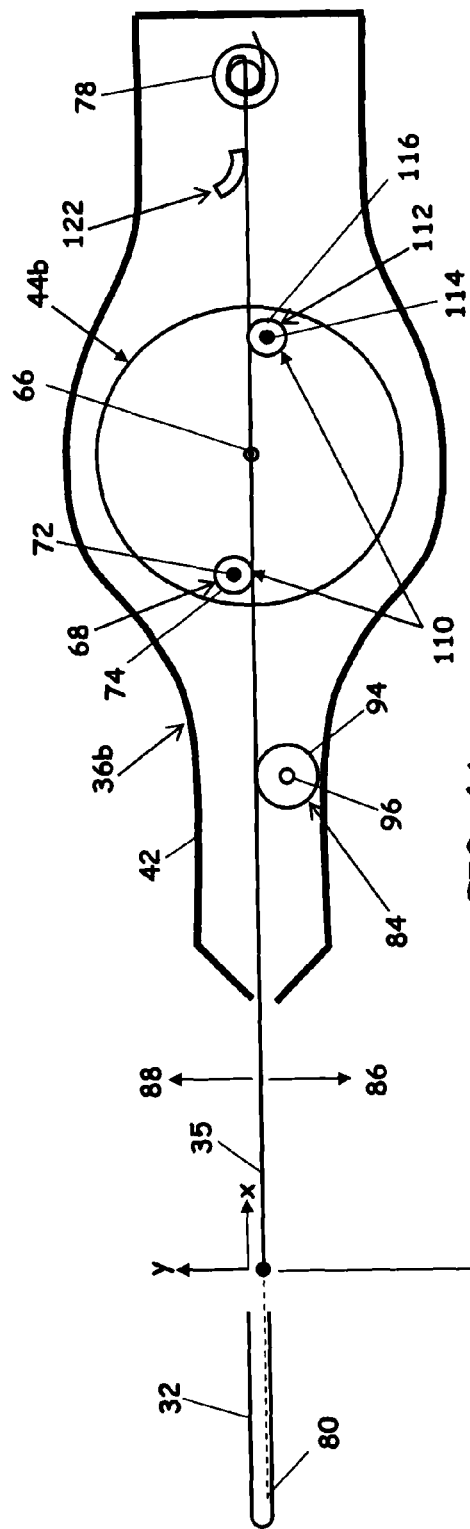
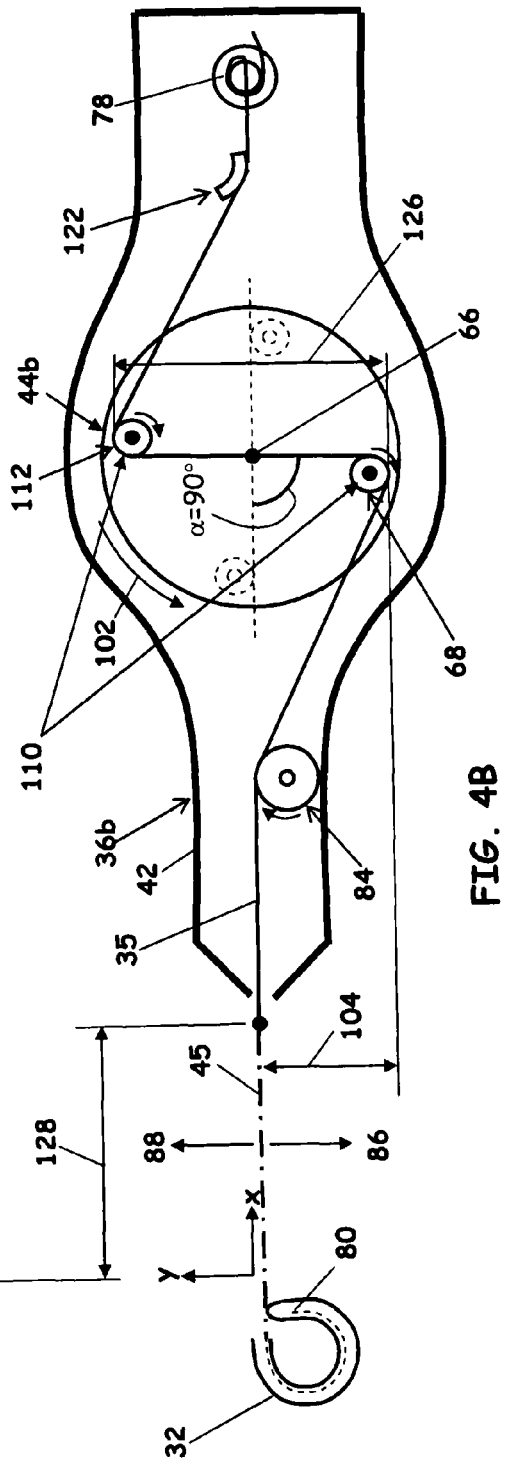
FIG. 4A
FIG. 4B

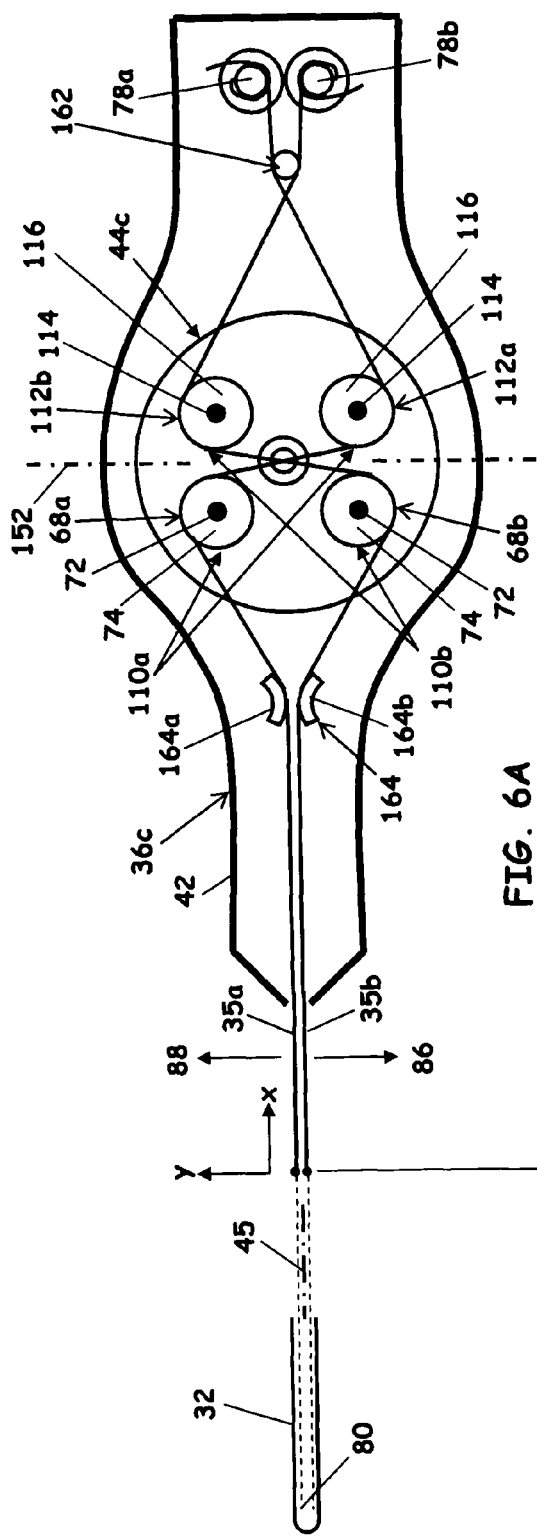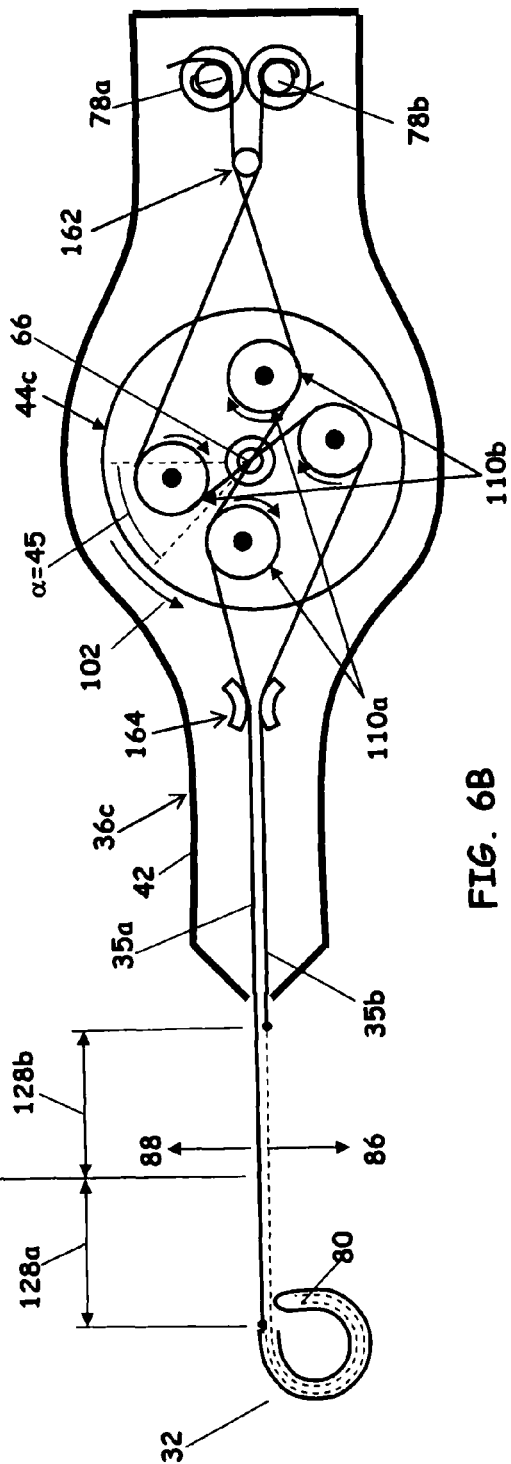
FIG. 6A
FIG. 6B

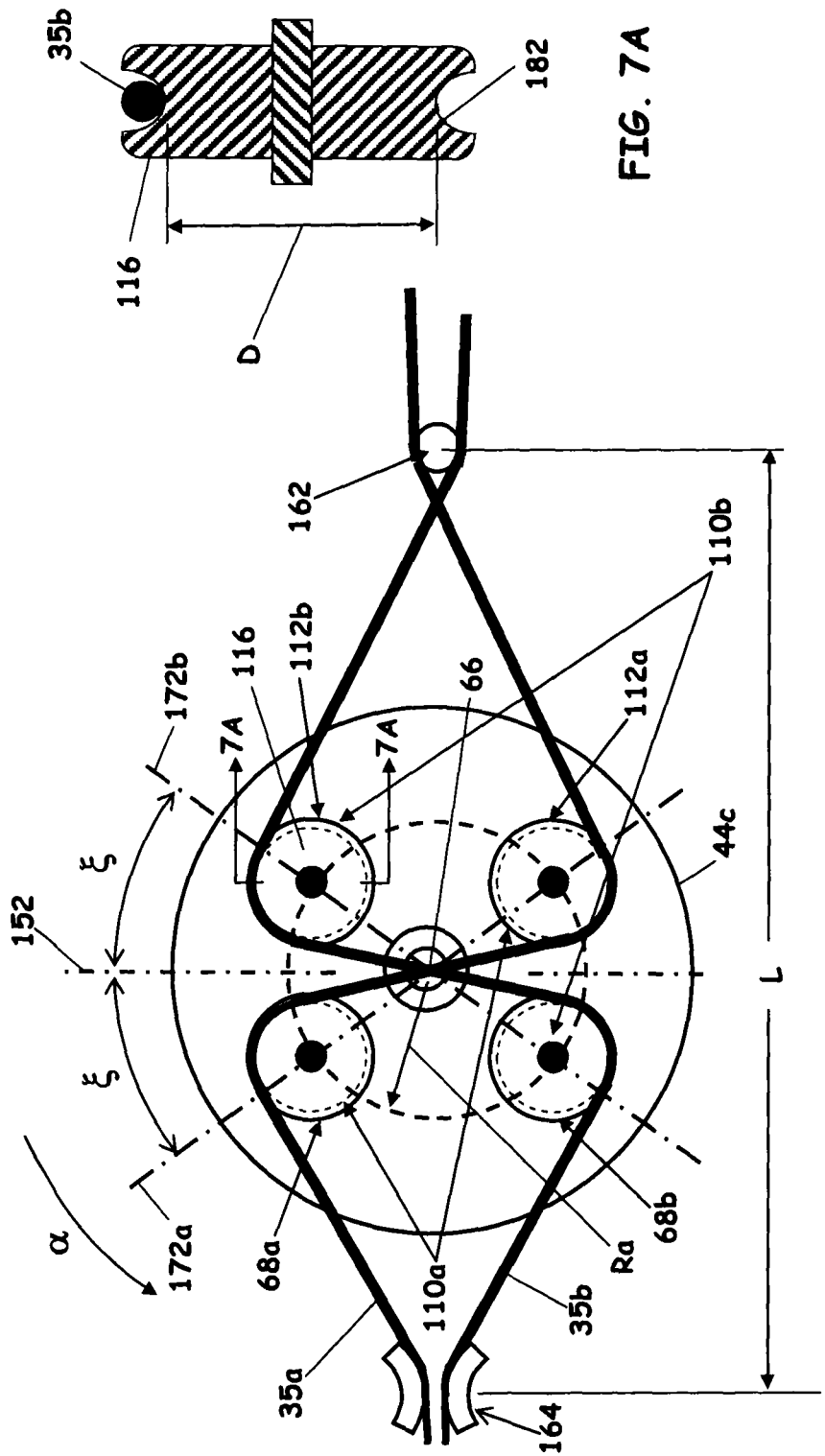

STEERING CONTROL MECHANISMS FOR CATHETERS

FIELD OF THE DISCLOSURE

The invention is generally directed to catheters. More specifically, the invention is directed to a control handle adapted to control the deflection of steerable catheter.

BACKGROUND OF THE DISCLOSURE

Catheter ablation is a surgical procedure in which a catheter having an ablation tip is fed through various biological lumens to reach targeted tissue within the body. Radiofrequency current ("RF current") is transmitted through electrodes disposed within the biological lumen and emitted from the ablation tip into the targeted tissue. The ablation tip is placed in close proximity to or in contact with the targeted tissue to maximize the amount of RF current supplied directly to the targeted tissue and limit the amount of untargeted tissue exposed to the RF current. Because the ablation catheter is navigated through existing biological lumen to reach the targeted tissue, catheter ablation surgery is less invasive than other available surgical techniques for reaching the targeted tissue, such as open heart surgery.

However, biological lumens and particularly blood vessels are often circuitous in nature and typically intersect many other biological lumens, presenting challenges with respect to catheter navigation therethrough. In order to reach the targeted tissue, the ablation tip must be threaded through the bends in the biological lumen and through the various intersections to reach the targeted tissue. Once near the target tissue, the operator must be able to accurately position the tip of the catheter for adequate delivery of the ablation energy. The difficult navigation process required can extend the surgical time considerably and can result in injury to the patient.

Catheter bodies often comprise an internal pull wire for deflecting the tip of the catheter body to more easily navigate the various turns and bends of the biological lumen. The pull wire is typically affixed proximate the tip of the catheter body and extends through the catheter body exiting the end of the catheter body that remains outside the patient's body. An operator can apply a pulling force to the pull wire to cause the tip of the catheter to deflect. Handles are often affixed to the proximal end of the catheter body to manipulate the pull wire for control of the defection of the catheter. However, different operators often have different tactile preferences as to the amount of force required to deflect the tip of the catheter a given amount. A standardized or factory set force-to-deflection relationship may cause some operators to over-deflect the catheter tip (thus denying the operator resolution in deflecting the tip), while causing others discomfort because the force requirement for a given tip deflection is uncomfortably high.

One steering mechanism used for deflection of a catheter tip is the so-called "steering spine." Steering spines are characterized by a continuous portion (i.e. the "spine") that extends from the proximal to the distal end of the steering mechanism. An advantage of the steering spine is that the resilience or elasticity of the continuous spine portion generates its own restorative force when the spine is deflected from its at-rest position, thus negating the need for a second pull wire to restore the tip to a straightened geometry. However, the deflection steering spines implementing a single pull wire are "unidirectional"—i.e., can only deflect in one direction relative to the steering spine (typically away from the steering spine). Thus, deflecting the catheter tip in a direction opposite an instant orientation of the steering spine (i.e., in the direction towards the instant orientation of the steering spine) requires first rotating the entire catheter assembly 180° about its longitudinal axis.

Other catheters utilize steering systems that are "bi-directional," i.e., capable of deflecting in two directions. These systems typically implement two pull wires. Often, the tip deflection mechanism does not include a steering spine, so there is no passive or elastic restorative force. Instead, some bi-directional steering systems rely on the pulling action of the second pull wire to actively restore or reverse the action of the first pull wire, and vice-versa.

Certain catheter handles include tactile feedback mechanisms, such as vibrators, to inform the user when a certain condition has been met. An example of such tactile feedback mechanisms are disclosed in U.S. Patent Application Publication No. 2011/0251554 to Romoscanu, assigned to the owner of the present patent application and the disclosure of which is incorporated by reference herein except for the claims and express definitions contained therein.

A device that can accommodate the tactile preferences of an individual operator in the control of catheter tip deflection would be welcome. A frictional device that can substantially match the varying restorative force of the steering spine across the range of tip deflection while reducing the force requirements at low tip deflections would also be welcome. A catheter system that implements non-auditory sensory perceptions would also find utility in the modern operating MOM.

SUMMARY OF THE DISCLOSURE

Various embodiments of the invention comprise a catheter handle having a thumb knob arrangement for manipulating a pull wire or pull wires that steer the distal end of a catheter. The internal arrangement of the catheter provides increased axial displacement of the pull wire per unit rotation of the thumb knob, thereby increasing the effective stroke of the thumb knob. Different embodiments of the catheter handle can be configured for uni-directional steering (i.e., actuation of a single pull wire) or bi-directional steering (i.e., alternating actuation of two pull wires).

The bi-directional steering embodiments can be configured to simultaneously take in one of the pull wires while releasing the other of the pull wires in a quasi-linear fashion. When the thumb knob is rotated in a first rotational direction, a first of the pull wires is taken in by the handle and placed in tension, causing the distal end of the catheter to deflect towards a first lateral direction, while a second of pull wires is released, thereby being put in a state of no tension or reduced tension so as reduce resistance to the desired deflection in the first lateral direction. When the rotational direction of the thumb knob is reversed, the role of the wires is reversed, i.e., the second wire is put in tension while the first wire is released.

In one bi-directional embodiment, the quasi-linear aspect of the wire intake and release enables the amount of wire taken in by the handle to be substantially equal to or less than the amount of wire released by the handle, regardless of the direction of rotation of the thumb knob. Functionally, this aspect of the invention further prevents the released wire from opposing the action of the tensioned wire, and also provides an operating margin that allows for imperfections in the system, such as differential changes in the axial deformations of the pull wires due the changing tortuousness catheter in situ.

Structurally, various embodiments of the invention include a control handle for a steerable catheter, the control handle comprising a housing having a proximal end and a distal end and defining an actuation axis that passes thorough the proximal end and the distal end. A cam assembly is disposed within the housing, the cam assembly being rotatable about a rotation axis. In some embodiments, the cam assembly includes a cam and a first dual pin set including a first pin assembly and a second pin assembly, the first and second pin assemblies each defining a pin axis that is parallel to the rotation axis. The first and second pin assemblies are mounted to the cam and, in one embodiment, are diametrically opposed about the rotation axis and centered at a centering radius from the rotation axis. In certain embodiments, a first guide is coupled to the housing and located proximal to the cam assembly, and a second guide is coupled to the housing and located distal to the cam assembly. A first pull wire is anchored to the housing proximate the proximal end of the housing. The first pull wire can engage the first guide, the first pin assembly, the second pin assembly, and the second guide and extends beyond the distal end of the housing. The first pull wire can also be routed substantially through the rotation axis between the first pin assembly and the second pin assembly. In various embodiments, the first and second pin assemblies each include a pulley that rotates about the pin axis of the respective pin assembly. The first guide can include a guide pin and the second guide can include a dual guide structure.

In certain embodiments, rotation of the cam in a first direction about the rotation axis causes the first pull wire to wrap partially around both of the first pin assembly and the second pin assembly for axial displacement of the first pull wire in a proximal direction along the actuation axis. The rotation of the cam about the rotation axis in a second direction causes the first pull wire to unwrap partially around both of the first pin assembly and the second pin assembly for axial displacement of the first pull wire in a distal direction along the actuation axis.

In some embodiments of the invention, a "4-pin" cam assembly suitable for bi-directional operation comprises a second dual pin set including a first pin assembly and a second pin assembly. The first and second pin assemblies of the second dual pin set each define a pin axis that is parallel to the rotation axis. The first and second pin assemblies of the second dual pin set are mounted to the cam and can be diametrically opposed about the rotation axis and centered at a centering radius from the rotation axis. In one embodiment, the first dual pin set and the second dual pin set are of mirrored symmetry about a plane of symmetry, the plane of symmetry passing through the rotational axis and being substantially orthogonal to the actuation axis. In this embodiment, a second pull wire is anchored to the housing proximate the proximal end of the housing. The second pull wire can engage the first guide, the first pin assembly of the second pin set, the second pin assembly of the second pin set, and the second guide and extend beyond the distal end of the housing. The second pull wire can be routed substantially through the rotation axis between the first pin assembly of the second pin set and the second pin assembly of the second pin set.

For the 4-pin cam assembly, rotation of the cam in the first direction about the rotation axis causes the second pull wire to unwrap partially around both of the first pin assembly of the second pin set and the second pin assembly of the second pin set for axial displacement of the second pull wire in the distal direction along the actuation axis. Rotation of the cam about the rotation axis in the second direction also causes the second pull wire to wrap partially around both of the first pin assembly of the second pin set and the second pin assembly of the second pin set for axial displacement of the second pull wire in the proximal direction along the actuation axis.

In certain embodiments of the invention, a first amount of the first pull wire taken in by the cam assembly is less than a second amount of the second pull wire released by the cam assembly over a first range of rotation angles. Also, the first amount of the first pull wire taken in by the cam assembly can be substantially equal to the second amount of the second pull wire released by the cam assembly over a second range of rotation angles.

BRIEF DESCRIPTION OF THE FIGURES

FIG. 1 is a schematic of the components of a catheter system according to an embodiment of the invention;

FIG. 1A is a schematic of a robotic manipulator in an embodiment of the invention;

FIG. 2 is a perspective view of a catheter handle in an embodiment of the invention;

FIG. 2A is an enlarged, partial plan view of the catheter of FIG. 2;

FIGS. 4A and 4B are schematic views of a uni-directional control handle having a set of dual pins for actuating a single pull wire in an embodiment of the invention;

FIGS. 6A and 6B are schematic views of the bi-directional control handle of FIG. 6;

FIG. 7 is a schematic of the cam assembly of the bi-directional control handle of FIG. 6;

FIG. 7A is a sectional view of a pin assembly of the cam assembly of FIG. 7.

DETAILED DESCRIPTION OF THE FIGURES

Figure 2B:
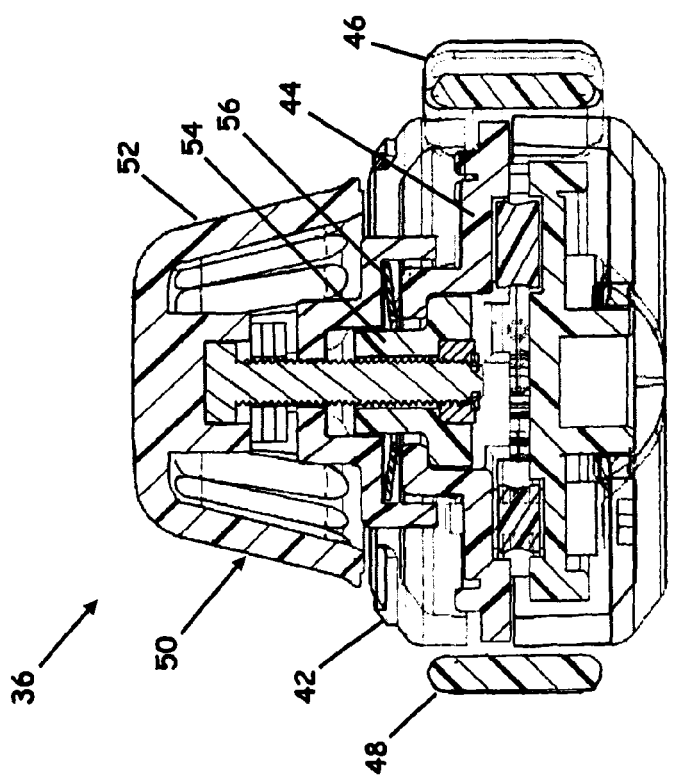
FIG. 2B is a sectional view of the catheter of FIG. 2.

Referring to FIG. 1, a catheter system 20 is depicted in an embodiment of the invention. The catheter system 20 comprises an elongated catheter assembly 22 having a proximal portion 24, a middle portion 26 and a distal portion 28. The distal portion of catheter assembly 22 includes a steering section 32 and an end effector 34. The catheter system 20 can be equipped with instrumentation for determination of at least one operating condition of catheter assembly 22. Examples of operating parameters upon which the operating condition can be predicated includes a force, a temperature, a timer that provides a duration or delay, and/or an irrigation flow. In some embodiments, the instrumentation is disposed in end effector 34. Steering section 32 further comprises one or more pull wires 35 (depicted in the various figures) disposed within elongated catheter assembly 22 and affixed to the distal end of steering section 32, wherein applying a pulling force to one of the pull wires causes steering section 32 to deflect. In one embodiment, the steering section 32 comprises a steering spine (not depicted). In other embodiments, the steering section 32 comprises a series of jointed segments or a flexible tube (neither depicted). In one embodiment, proximal portion 24 is operatively coupled with a control handle 36 that includes a cam assembly 37 for manipulating the pull wire(s) 35.

The control handle 36 can be operatively coupled with a controller 38 containing various appurtenances that augment the operation of the catheter system 20. Non-limiting examples of the appurtenances of controller 38 include power sources and/or irrigation systems for sourcing the end effector 34, optical sources for sourcing fiber optic systems within the catheter system 20, data acquisition devices for monitoring instrumentation of the catheter system 20, and/or control systems for controlling the sourcing of the end effector 34. The controller 38 can be configured to receive input signals from the catheter assembly 22 and to produce output signals to catheter assembly 22. The controller 38 can be coupled to control handle 36 via instrumentation leads, power source leads, irrigation lines, fiber optics and/or wireless transmission.

In some embodiments, the instrumentation can include a force sensing assembly contained within or operatively coupled with end effector 34 for detection of contact force between an organ or vessel and end effector 34. Non-limiting examples of force sensing assemblies are disclosed at U.S. Patent Application Publication Nos. 2006/200049, 2007/060847, 2008/0294144, 2009/287092, and 2009/177095 to Leo et al. and U.S. Patent Application Publication No. 2008/009750 to Aeby et al., all of which are assigned to assignee of this application, and the disclosures of which are hereby incorporated by reference in their entirety herein except for express definitions contained therein.

In another example, end effector 34 can be fitted with an ablation head coupled to an energy source (not depicted). The energy source can be located within the controller 38. In some embodiments, controller 38 can include analog electronic components to execute the control logic required to monitor operational parameters. In still other embodiments, the controller 38 includes both analog and digital components for this purpose. The controller 38 can comprise a general purpose computer, or a specialized console configured for operation only with catheter system 20.

Referring to FIG. 1A, an alternative embodiment is depicted wherein the cam assembly 37 is included as part of in a robotic manipulator 40 that is coupled with the controller 38 and the catheter assembly 22. In this embodiment, the robotic manipulator 40 controls the action of the cam assembly 37, thereby controlling the deflection of the steering section 32 and end effector 34. The robotic manipulator 40 can be configured to receive commands from the controller 38. While the balance of this patent application is directed to control handles, the skilled artisan will recognize the applicability of the disclosed arrangements as being adaptable to robotic manipulators. Accordingly, discussions herein directed to control handles are also applicable to robotic manipulators mutatis mutandis.

Referring to FIGS. 2, 2A and 2B, the control handle 36 is depicted in an embodiment of the invention. The control handle 36 includes a housing 42 having a proximal end 41 and a distal end 43 and defining an actuation axis 45 passing through the proximal and distal ends 41 and 43. The housing 42 contains a cam 44 operatively coupled with a pair of diametrically opposed thumb knobs 46 and 48. The thumb knobs 46 and 48 can be of different shape. In the depicted embodiment, thumb knob 46 defines a substantially semicircular profile, whereas thumb knob 48 defines a divoted profile.

A friction adjustment mechanism 50 can also be operatively coupled to the cam 44. The friction adjustment mechanism includes an adjustment knob 52 threadably engaged with a collar 54 that disposed within the cam 44. A biasing element 56, such as a wave washer or spring washer, is disposed between the collar 54 and the housing 42.

In operation, the cam 44 is rotated in either direction about a rotation axis 66. The thumb knobs 46 and 48, being of different profiles, have different tactile qualities, so that the operator can tell which knob is in contact with his or her thumb without looking at the handle. The adjustment knob 52 can be rotated to adjust the compression exerted by the collar 54 on the biasing element 56. The frictional resistance to the rotation of the cam 44 can be governed primarily by the friction between the collar 54 and the biasing element 56. In this way, the friction associated with rotating the cam 44 can be adjusted according to the preference of the operator.

Figure 3A:
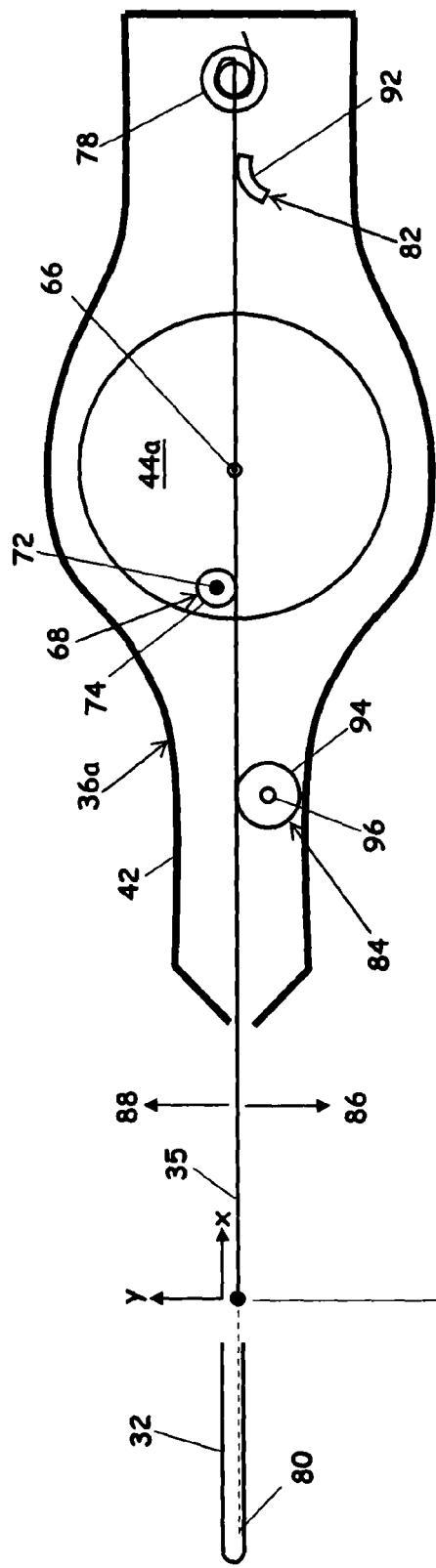
FIGS. 3A and 3B are schematic views of a uni-directional control handle having a single pin assembly for actuating a single pull wire in an embodiment of the invention.
Figure 3B:
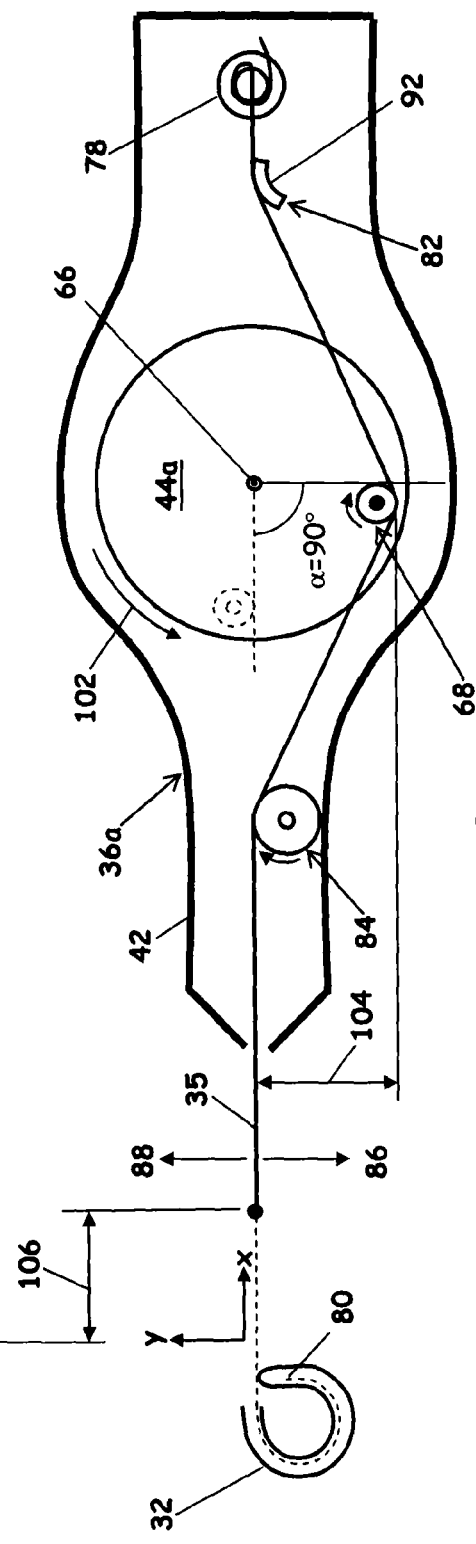

Referring to FIGS. 3A and 3B, a "single pin" control handle 36a is depicted in an embodiment of the invention. The control handle 36a includes a housing 42 that contains a cam 44a rotatable about a rotation axis 66. The single pulley control handle 36a is so-named because it includes a single pin assembly 68 that actuates the pull wire 35. The single pin assembly 68 includes a pin operably mounted to the cam 44a and defines a pin axis 72 that is radially offset from and substantially parallel to the rotation axis 66. In certain embodiments, the pin assembly 68 includes a pulley 74 that rotates about the pin axis 72.

The pull wire 35 is mounted to an anchor 78 affixed to the housing 42 proximal to the cam 44a, the pull wire 35 being routed past the cam 44a and extending out of the housing 42 distal to the cam 44a, terminating at a distal portion 80 of the steering section 32. In one embodiment, the pull wire 35 engages pair of guides, a contoured guide 82 that is proximal to the cam 44a and a guide pin assembly 84 that is distal to the cam 44a. The contoured guide 82 and guide pin assembly 84 are located in a first lateral direction 86 relative to the pull wire 35. The pin assembly 68 or, when utilized, the pulley 74 also engages the pull wire 35 and is located in a second lateral direction 88 relative to the pull wire 35. The first and second lateral directions 86 and 88 are opposite each other and orthogonal to the rotation axis 66.

In one embodiment, one or both the contoured guide 82 and guide pin assembly 84 comprise a static member 92 such as an arcuate segment (as depicted for contoured guide 82 in FIGS. 3A and 3B) or a shaft. One or both of the contoured guide 82 and guide pin assembly 84 can also comprise a pulley 94 operably mounted to the shaft 96 (as depicted for guide pin assembly 84 in FIGS. 3A and 3B).

In operation, the cam 44a is rotated in a first direction 102 at an angle α, causing the pin assembly 68 to impose a lateral deflection 104 on the pull wire 35 in the first lateral direction 86 between the contoured guide 82 and guide pin assembly 84. (The angle α is depicted at 90° in the depiction of FIG. 3B.) The deflection 104 causes an axial displacement 106 of the pull wire 35. The pin assembly 86 translates along the pull wire 35. For configurations where the pin assembly 86 does not include a pulley (not depicted), the pin of the pin assembly 86 slides along the pull wire 35 as the cam 44a is rotated through the angular displacement α; for configurations including the pulley 74 (as depicted in FIG. 3B), the pin assembly 86 rolls along the pull wire 35. The axial displacement 106 also causes the pull wire 35 to slide or roll across the guide pin assembly 84, and to partially wrap around the contoured guide 82.

For the control handle 36a, only the lateral deflection 104 affects the axial displacement 106 of the pull wire 35. That is, because the pin assembly 86 does not grip the pull wire 35, but instead slides or rolls along the pull wire 35, there is no component of the axial displacement 106 that is attributed to the movement of the pin assembly 86 in the axial direction (i.e., parallel to the "x-axis" depicted in FIGS. 3A and 3B). Accordingly, the axial displacement 106 is generally proportional to SIN(α).

Referring to FIGS. 4A and 4B, a "two pin" or "dual pin" control handle 36b is depicted in an embodiment of the invention. The control handle 36b includes many of the same aspects as control handle 36a, indicated by identical numerical references. The cam 44b of control handle 36b further includes a second pin assembly 112 diametrically opposed to the (first) pin assembly 68 to present a set of dual pins 110, referred to alternatively as dual pin set 110. The two pin control handle 36b is so-named because there are two pin assemblies 68 and 112 that are engaged with and actuate the pull wire 35.

The second pin assembly 112 is disposed in the first lateral direction 86 relative to the pull wire 35 and in contact with the pull wire 35. The second pin assembly 112 includes a pin that defines a pin axis 114 and, in one embodiment, includes a pulley 116 that rotates about the pin axis 114. Control handle 36b includes a first contoured guide structure 122 in contact with pull wire 35. The contoured guide structure 122 can be similar to the contoured guide 82 of control handle 36a, except that contoured guide 122 is located in the second lateral direction 88 relative to the pull wire 35.

In operation, when the cam 44b is rotated in the first direction 102 at the angle α, the first pin assembly 68 imposes the lateral deflection 104 on the pull wire 35 in the first lateral direction 86, just as with control handle 36a (described above attendant to FIG. 3B). In addition, the second pin assembly 112 also translates along the pull wire 35, imposing an additional, second lateral deflection 126 in the second lateral direction 88. Note that the second lateral deflection 126 is taken relative to the first pin assembly 68, and not the original or "at rest" position of the pull wire 35. This is because the "additional" lateral deflection 126 is relative to the actuated position for control handle 36a depicted in FIG. 3B. Accordingly, for the depicted embodiment of the control handle 36b, where the first and second pin assemblies 68 and 112 are diametrically opposed and at substantially equal radii from the rotation axis 66, the additional lateral deflection 126 of the pull wire 35 is about twice that of the (first) lateral deflection 104 at a deflection angle α of 90°. The combined deflections 104 and 126 causes an axial displacement 128 of the pull wire 35 along the actuation axis 45.

Figure 5:
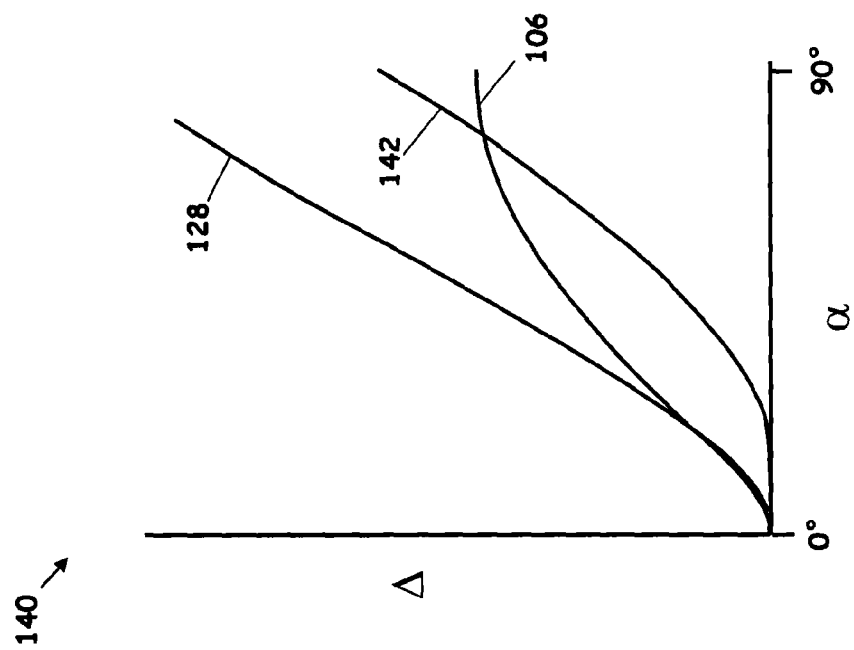
FIG. 5 is a graph of the axial displacement Δ of the single pull wire vs. the rotation angle α of the cam for the single pin and dual pin arrangements of FIGS. 3 and 4.

Referring to FIG. 5, a graph 140 illustrating the axial deflections 106 and 128 of the pull wire 35 (designated by the symbol Δ on the ordinate) as a function of the cam rotation angle α is depicted in an embodiment of the invention. The axial deflection 128 is the sum of the axial deflection 106 caused by the lateral displacement 104 of the first pin assembly 68, and a second axial deflection 142 caused by the lateral displacement 126 of the second pin assembly 112. That is, the quasi-linear axial deflection 128 is actually the confluence of two non-linear axial deflections—the sinusoidal axial deflection 106 and the complementary deflection 142.

Figure 6:
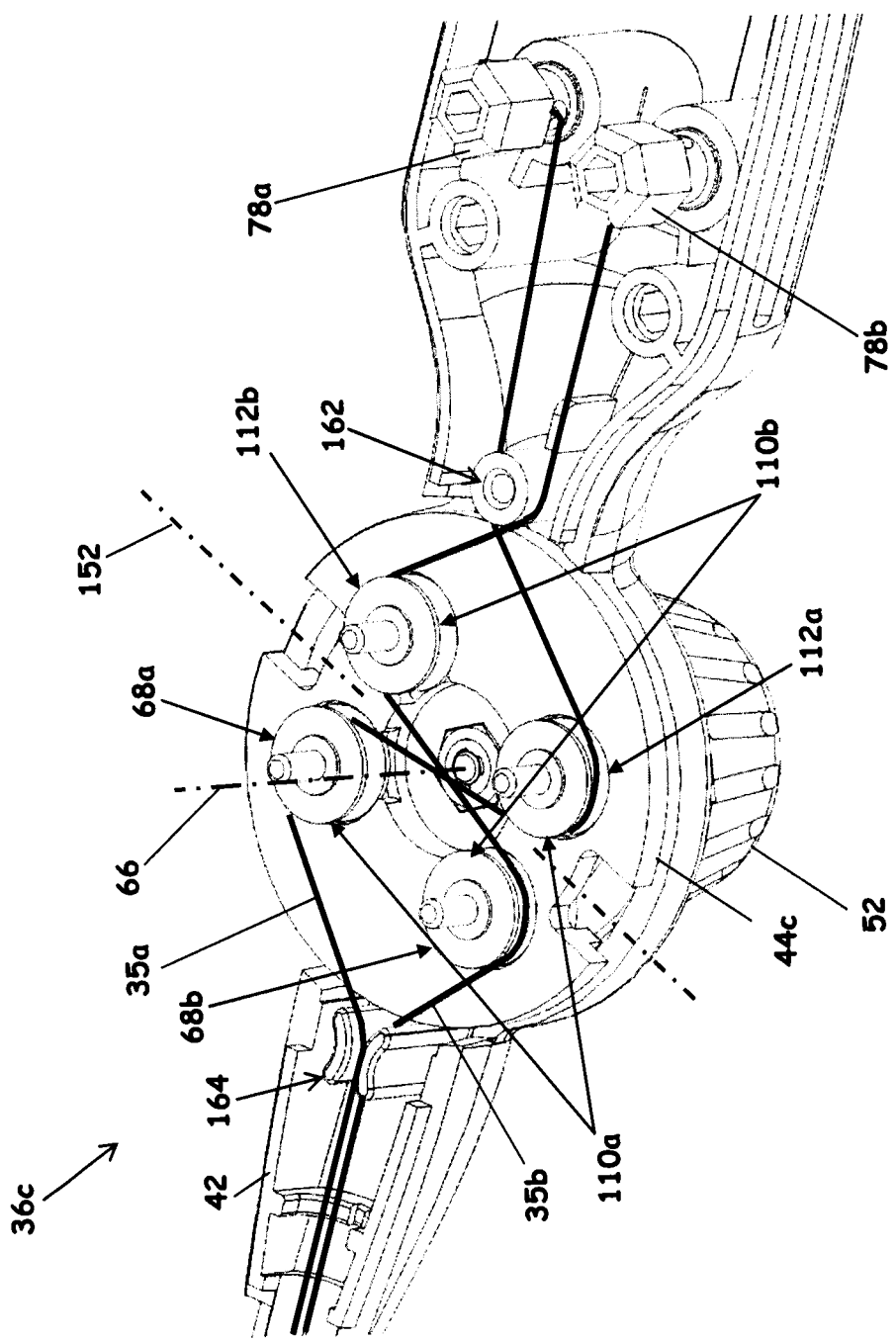
FIG. 6 is a bottom partial isometric view of a bi-directional control handle with the bottom cover removed, the bi-directional control handle including a pair of dual pin sets for actuating dual pull wires in an embodiment of the invention.

Referring to FIGS. 6A and 6B, a "four pin" catheter handle assembly 36c is depicted in an embodiment of the invention. The control handle 36b includes many of the same aspects as control handles 36a and 36b, indicated by identical numerical references. The four pin catheter handle assembly 36c includes two sets of dual pins 110a and 110b, each engaged with a respective pull wires 35a and 35b. The four-pin handle assembly is so-named because each dual pin set 110a, 110b includes a first pin assembly 68a, 68b and a second pin assembly 112a, 112b, for a total of four pin assemblies to actuate the two pull wires 35a and 35b. In one embodiment, the dual pin sets 110a and 110b are of mirrored symmetry about a plane of symmetry 152 that passes through the rotation axis 66 of the cam 44c, the plane of symmetry 152 being substantially perpendicular to the axial direction (i.e., perpendicular to the "x-axis").

Each dual pin set 110a, 110b operates in the same manner and has same operating characteristics the dual pin set 110 of control handle 36b (including the quasi-linear axial deflection characteristics depicted at FIG. 5), however in opposite directions. That is, if cam 44c is rotated so that dual pin set 110b applies a tension to pull wire 35b (as depicted in FIG. 6B), then dual pin set 110a simultaneously releases pull wire 35a. The amount of wire released by the dual pin set 110a translates to an axial displacement 128a in a distal direction relative to the handle 36c, while the amount of wire taken in by the dual pin set 110b translates to an axial displacement 128b. Conversely, if cam 44c is rotated so that dual pin set 110a applies a tension to pull wire 35a, then dual pin set 110b simultaneously releases pull wire 35b, which would reverse the directions of the axial displacements 128a and 128b.

Additional structure for the control handle includes guides that capture both pull wires 35a and 35b. A guide pin 162 can serve to capture both pull wires 35a and 35b by virtue of being disposed therebetween. A dual guide structure 164 can also be utilized that includes two opposed contour guides 164a and 164b, each being similar to contoured guides 82 and 122.

Referring to FIGS. 7 and 7A, various governing parameters that determine the operating characteristics of the four pin catheter handle assembly 36c are depicted in an embodiment of the invention. The governing parameters include an angle 4 between the plane of symmetry 152 and each of a first coordinate 172a and second coordinate 172b along which dual pin assemblies 110a and 110b, respectively, are centered. The governing parameters also include a centering radius Ra centered about the rotation axis 66 at which each of the pin assemblies 68a, 68b, 112a and 112b are centered, a tangential contact diameter D of the pin assemblies 68a, 68b, 112a and 112b, and a pivot centering dimension L, defined as the distance between the centers of guides 162 and 164. In certain embodiments, the tangential contact diameter D of a given pin assembly is less than an overall diameter of the pin assembly. For example, for embodiments utilizing pulleys 74 and/or 116, a minimum or inner diameter defined by a tangential groove 182 for registering the pull wire within the pulley 74, 116 defines the tangential contact diameter D (FIG. 7A).

Mathematical formulae describing the equivalent axial displacements 128a and 128b are presented in Eqns. (1) and (2) for an embodiment of the invention. The equivalent axial displacement 128a of the released pull wire 35a is expressed by the following equation:

$$ReleasedWire(\alpha) = \qquad \text{Eqn. (1)}$$

$$-2Rp\left(\alpha + \sin^{-1}\left(\frac{Rp}{\sqrt{(Ra\cos(\xi))^2 + (Lf - Ra\sin(\xi))^2}}\right)\right) -$$

$$\sin^{-1}\left(\frac{Rp}{\sqrt{(Ra\cos(\alpha+\xi))^2 + (Lf - Ra\sin(\alpha+\xi))^2}}\right) +$$

$$\tan^{-1}\left(\frac{Ra\cos(\xi)}{Lf - Ra\sin(\xi)}\right) - \tan^{-1}\left(\frac{Ra\cos(\alpha+\xi)}{Lf - Ra\sin(\alpha+\xi)}\right) -$$

$$2\sqrt{-Rp^2 + (Ra\cos(\xi))^2 + (Lf - Ra\sin(\xi))^2} +$$

$$2\sqrt{-Rp^2 + (Ra\cos(\alpha+\xi))^2 + (Lf - Ra\sin(\alpha+\xi))^2}$$

where Rp is the pulley radius (Rp=D/2), Ra is the centering radius, ξ the angle of the pulley axis relative to the plane of symmetry 152 the catheter is in a neutral position, Lf is the distal or proximal fixed pin distance from the cam (Lf=L/2), and α is the rotational displacement of the cam relative to the neutral position.

Likewise, the equivalent axial displacement 128b of the pull wire 35a taken in by the cam is expressed by the following equation:

$$PulledWire(\alpha) = \qquad \text{Eqn. (2)}$$
$$2Rp\left(\alpha + \sin^{-1}\left(\frac{Rp}{\sqrt{(Ra\,\cos(\alpha-\xi))^2 + (Lf + Ra\,\sin(\alpha-\xi))^2}}\right) - \sin^{-1}\left(\frac{Rp}{\sqrt{(Ra\,\cos(\xi))^2 + (Lf - Ra\,\sin(\xi))^2}}\right) + \tan^{-1}\left(\frac{Ra\,\cos(\alpha-\xi)}{Lf - Ra\,\sin(\alpha-\xi)}\right) - \tan^{-1}\left(\frac{Ra\,\cos(\xi)}{Lf - Ra\,\sin(\xi)}\right)\right) + 2\sqrt{-Rp^2 + (Ra\,\cos(\alpha-\xi))^2 + (Lf + Ra\,\sin(\alpha-\xi))^2} - 2\sqrt{-Rp^2 + (Ra\,\cos(\xi))^2 + (Lf - Ra\,\sin(\xi))^2}$$

The governing parameters can further be characterized in dimensionless term by establishing the centering radius R as the characteristic length of the system. Accordingly, one can define a dimensionless tangential contact diameter $D^* = D/R$ and a dimensionless pivot centering dimension $L^* = L/R$, the angle ξ already being dimensionless. Generally, assemblies having combinations where the dimensionless parameters included in the approximate ranges of $2.0 \leq L^* \leq 2.2$, $0.39 \leq D^* \leq 0.41$ and $34° \leq \xi \leq 36°$ possess the desired operating characteristics.

The operating parameters of the four pin catheter handle assembly 36c can be configured so that the cam 44c releases as much or slightly more of the released pull wire than it takes in of the actuated pull wire. Consider a system where the opposite is true (i.e., the amount of pull wire released by the cam 44c is less than the amount taken in): in this scenario, the released wire will be put under a tension, thereby countering to some extent the desired deflection of the steering section 32 of the catheter assembly. Accordingly, it is preferable that the cam 44c release as much or slightly more wire than it takes in.

Figure 8:
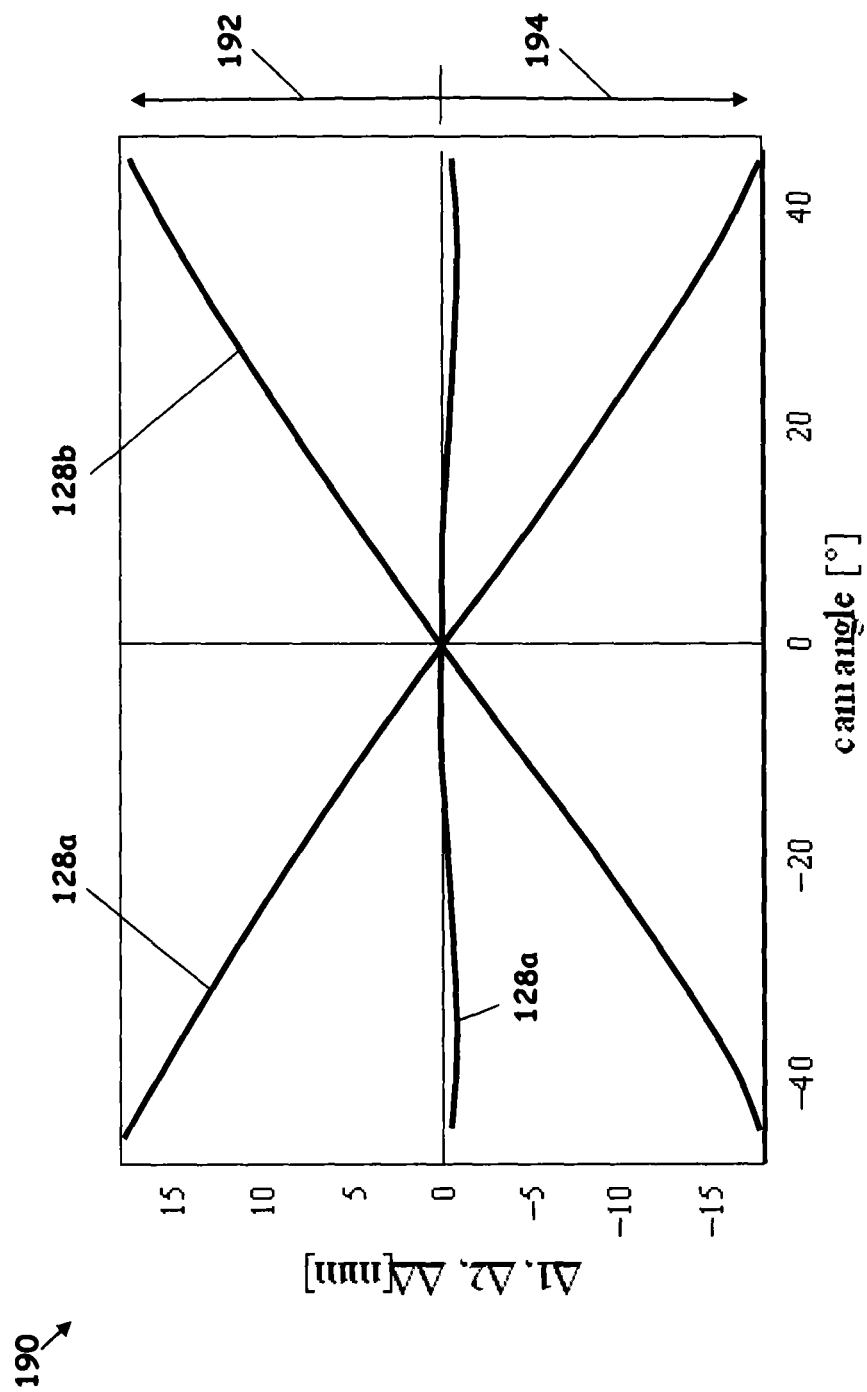
FIG. 8 is a graph of the axial displacement Δ of the dual pull wires vs. the rotation angle α of the cam for the single pin and dual pin arrangement of FIG. 6 in an embodiment of the invention.

Referring to FIG. 8, a graph 190 of the predicted operating characteristics of the four pin catheter handle assembly 36c is depicted in an embodiment of the invention. The dimensionless governing parameters upon which the graph 190 is based are $L^* = 2.073$, $D^* = 0.3974$ and $\xi = 35°$, with the characteristic length R at 19.50 mm. The graph 190 presents the rotation angle α or "cam angle" of the cam 44c on the abscissa and the predictions of the axial displacements 128a and 128b (labeled as Δ1 and Δ2 on the ordinate) of pull wires 35a and 35b, respectively, on the ordinate. The ordinate of the graph has a positive range 192 and a negative range 194. The positive range 192 corresponds to an extension of the respective pull wire (i.e., wire being released by the cam 44c) while the negative range 194 corresponds to a retraction of the respective pull wire (i.e., wire being taken in by the cam 44c). A difference 196 between the magnitudes of the values in the positive range 192 and the negative range 194 as a function of α is also presented (labeled as ΔΔ on the ordinate). The difference 196 is obtained by taking the difference between the magnitudes of Eqns. (1) and (2).

The difference 196 is either substantially zero or slightly negative, depending on the cam angle. This result indicates that the amount of wire released by the cam 44c is predicted to be either the same or slightly more than the amount of wire taken in by the cam 44c, which, as discussed above, is a desirable result.

Each of the features and methods disclosed herein may be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the invention, it is expressly intended that the provisions of Section 112, sixth paragraph of 35 U.S.C. are not to be invoked unless the specific terms "means for" or "step for" are recited in the subject claim.

What is claimed is:

1. A control handle for a steerable catheter, the control handle comprising:
   a housing having a proximal end and a distal end and defining an actuation axis that passes thorough said proximal end and said distal end;
   a cam assembly disposed within said housing, said cam assembly being rotatable about a rotation axis and including:
      a cam, and
      a first dual pin set, said first dual pin set including a first pin assembly and a second pin assembly, said first and second pin assemblies each defining a pin axis that is parallel to said rotation axis, said first and second pin assemblies being mounted to said cam and being diametrically opposed about said rotation axis and centered at a centering radius from said rotation axis;
   a first guide coupled to said housing and being located proximal to said cam assembly;
   a second guide coupled to said housing and being located distal to said cam assembly; and
   a first pull wire anchored to said housing proximate said proximal end of said housing, said first pull wire engaging said first guide, said first pin assembly, said second pin assembly, and said second guide and extending beyond said distal end of said housing, said first pull wire being routed substantially through said rotation axis between said first pin assembly and said second pin assembly,
   wherein rotation of said cam in a first direction about said rotation axis causes said first pull wire to wrap partially around both of said first pin assembly and said second pin assembly for axial displacement of said first pull wire in a proximal direction along said actuation axis, and
   wherein said rotation of said cam about said rotation axis in a second direction causes said first pull wire to unwrap partially around both of said first pin assembly and said second pin assembly for axial displacement of said first pull wire in a distal direction along said actuation axis.

2. The control handle of claim 1, further comprising:
   a second dual pin set including a first pin assembly and a second pin assembly, said first and second pin assemblies of said second dual pin set each defining a pin axis that is parallel to said rotation axis, said first and second pin assemblies of said second dual pin set being mounted to said cam and being diametrically opposed about said rotation axis and centered at a centering radius from said rotation axis, said first dual pin set and said second dual pin set being of mirrored symmetry about a plane of symmetry, said plane of symmetry passing through said rotational axis and being substantially orthogonal to said actuation axis;

a second pull wire anchored to said housing proximate said proximal end of said housing, said second pull wire engaging said first guide, said first pin assembly of said second pin set, said second pin assembly of said second pin set, and said second guide and extending beyond said distal end of said housing, said second pull wire being routed substantially through said rotation axis between said first pin assembly of said second pin set and said second pin assembly of said second pin set, wherein rotation of said cam in said first direction about said rotation axis causes said second pull wire to unwrap partially around both of said first pin assembly of the second pin set and said second pin assembly of second pin set for axial displacement of said second pull wire in said distal direction along said actuation axis, and wherein rotation of said cam about said rotation axis in said second direction causes said second pull wire to wrap partially around both of said first, pin assembly of said second pin set and said second pin assembly of said second pin set for axial displacement of said second pull wire in said proximal direction along said actuation axis.

3. The control handle of claim 2, wherein
a first amount of said first pull wire taken in by said cam assembly is less that a second amount of said second pull wire released by said cam assembly over a first range of rotation angles.

4. The control handle of claim 3, wherein
said first amount of said first pull wire taken in by said cam assembly is substantially equal to said second amount of said second pull wire released by said cam assembly over a second range of rotation angles.

5. The control handle of claim 1, wherein said first and second pin assemblies each include a pulley that rotates about said pin axis of the respective pin assembly.

6. The control handle of claim 1, wherein said first guide comprises a guide pin and said second guide comprises a dual guide structure.

* * * * *